United States Patent
Knickerbocker et al.

(10) Patent No.: US 12,014,816 B2
(45) Date of Patent: Jun. 18, 2024

(54) MULTI-SENSOR PLATFORM FOR HEALTH MONITORING

(71) Applicant: International Business Machines Corporation, Armonk, NY (US)

(72) Inventors: John Knickerbocker, Orange, NY (US); Bing Dang, Chappaqua, NY (US); Qianwen Chen, Chappaqua, NY (US); Leanna Pancoast, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 518 days.

(21) Appl. No.: 17/130,534

(22) Filed: Dec. 22, 2020

(65) Prior Publication Data

US 2022/0199235 A1  Jun. 23, 2022

(51) Int. Cl.
*G16H 40/20*   (2018.01)
*A61B 5/00*    (2006.01)
(Continued)

(52) U.S. Cl.
CPC ........... *G16H 40/20* (2018.01); *A61B 5/7264* (2013.01); *A61B 5/7275* (2013.01); *A61B 5/747* (2013.01);
(Continued)

(58) Field of Classification Search
CPC ........ G16H 40/20; G16H 40/67; G16H 40/40; G16H 10/60; G16H 50/70; G16H 50/20;
(Continued)

(56) References Cited

U.S. PATENT DOCUMENTS

| 10,646,144 B2 * | 5/2020 | Lamego ............... A61B 5/6832 |
| 2011/0213217 A1 * | 9/2011 | McKenna .......... A61B 5/14552 |
| | | 600/301 |

(Continued)

FOREIGN PATENT DOCUMENTS

| CN | 106055854 A | 10/2016 |
| CN | 109346190 A | 2/2019 |

(Continued)

OTHER PUBLICATIONS

S. Lee, B. Grundlehner, R. G. van der Westen, S. Polito and C. Van Hoof, "Nightingale V2: Low-power Compact-sized Multi-Sensor Platform for Wearable Health Monitoring," 2019 41st Annual International Conference of the IEEE Engineering in Medicine (Year: 2019).*

(Continued)

*Primary Examiner* — Evangeline Barr
*Assistant Examiner* — Patricia K. Edouard
(74) *Attorney, Agent, or Firm* — Stephen J. Walder, Jr.; Kristofer Haggerty

(57) ABSTRACT

A mechanism is provided in a data processing system to implement a multi-sensor health monitoring platform. The mechanism applies a machine learning model to predict patient needs and patient activity trends based on physiological features and activity features of the patient. The mechanism applies the machine learning model to predict energy requirements for a plurality of medical sensors based on the predicted patient needs and patient activity trends. The mechanism schedules recharging of the plurality of medical sensors based on the predicted energy requirements and identifying one or more sensors to set to an activate state based on the predicted patient needs and patient activity trends. The mechanism collecting sensor data from the one or more sensors and applies the machine learning model to (Continued)

generate a point-of-care recommendation based on the collected sensor data.

20 Claims, 6 Drawing Sheets

(51) Int. Cl.
| | | |
|---|---|---|
| G06N 20/00 | (2019.01) | |
| G06Q 10/1093 | (2023.01) | |
| G06Q 50/06 | (2024.01) | |
| G06Q 50/26 | (2024.01) | |
| G16H 10/60 | (2018.01) | |
| G16H 40/40 | (2018.01) | |
| G16H 40/67 | (2018.01) | |
| G16H 50/20 | (2018.01) | |
| G16H 50/70 | (2018.01) | |
| H04L 9/32 | (2006.01) | |

(52) U.S. Cl.
CPC ......... *G06N 20/00* (2019.01); *G06Q 10/1095* (2013.01); *G06Q 50/06* (2013.01); *G06Q 50/26* (2013.01); *G16H 10/60* (2018.01); *G16H 40/40* (2018.01); *G16H 40/67* (2018.01); *G16H 50/20* (2018.01); *G16H 50/70* (2018.01); *H04L 9/32* (2013.01); *A61B 2560/0214* (2013.01)

(58) Field of Classification Search
CPC .... G06N 20/00; A61B 5/7264; A61B 5/7275; A61B 5/747; A61B 2560/0214; G06Q 50/06; G06Q 50/26; H04L 9/32
See application file for complete search history.

(56) References Cited

U.S. PATENT DOCUMENTS

| | | | |
|---|---|---|---|
| 2012/0203491 A1* | 8/2012 | Sun ................... | A61B 5/0006 |
| | | | 702/108 |
| 2014/0081662 A1 | 3/2014 | Bradrick et al. | |
| 2014/0091749 A1* | 4/2014 | Nevins ................ | H02J 7/34 |
| | | | 320/103 |
| 2015/0105631 A1 | 4/2015 | Tran et al. | |
| 2015/0213222 A1 | 7/2015 | Amarasingham et al. | |
| 2015/0036562 A1 | 12/2015 | Hallwachs | |
| 2017/0140119 A1* | 5/2017 | Laha ................... | G06V 10/764 |
| 2017/0258401 A1* | 9/2017 | Volpe ................ | A61N 1/0484 |
| 2018/0090229 A1* | 3/2018 | Sanyal ................ | H04L 67/125 |
| 2018/0192965 A1 | 7/2018 | Rose et al. | |
| 2018/0308569 A1* | 10/2018 | Luellen ................ | G16H 20/10 |
| 2018/0333585 A1* | 11/2018 | Gaddam ............ | A61N 1/37252 |
| 2019/0046037 A1* | 2/2019 | Ramesh ................ | G16H 50/20 |
| 2019/0130332 A1* | 5/2019 | Janssen ................ | G01R 31/382 |
| 2019/0378619 A1* | 12/2019 | Meyer .................. | G16H 50/70 |
| 2020/0185107 A1* | 6/2020 | Cox ...................... | G16H 50/50 |
| 2020/0219616 A1* | 7/2020 | Swift .................... | G06N 20/20 |
| 2020/0289033 A1* | 9/2020 | Sivertsen ............. | G06N 20/00 |
| 2021/0058736 A1* | 2/2021 | Ghazzaoui ............ | H04W 4/80 |
| 2022/0262517 A1* | 8/2022 | Van Sickle ....... | H02J 13/00001 |

FOREIGN PATENT DOCUMENTS

| | | |
|---|---|---|
| CN | 110136822 A | 8/2019 |
| CN | 111447288 A | 7/2020 |

OTHER PUBLICATIONS

A. Karakra, F. Fontanili, E. Lamine and J. Lamothe, "HospiT'Win: A Predictive Simulation-Based Digital Twin for Patients Pathways in Hospital," 2019 IEEE EMBS International Conference on Biomedical & Health Informatics (BHI), Chicago, IL, USA, 2019, pp. 1-4, doi: 10.1109/BHI.2019.8834534. (Year: 2019).*

S. C. Mukhopadhyay, "Wearable Sensors for Human Activity Monitoring: A Review," in IEEE Sensors Journal, vol. 15, No. 3, pp. 1321-1330, Mar. 2015, doi: 10.1109/JSEN.2014.2370945. (Year: 2014).*

International Search Report and Written Opinion dated Feb. 11, 2022 for International Application No. PCT/CN2021/130093, 10 pages.

* cited by examiner

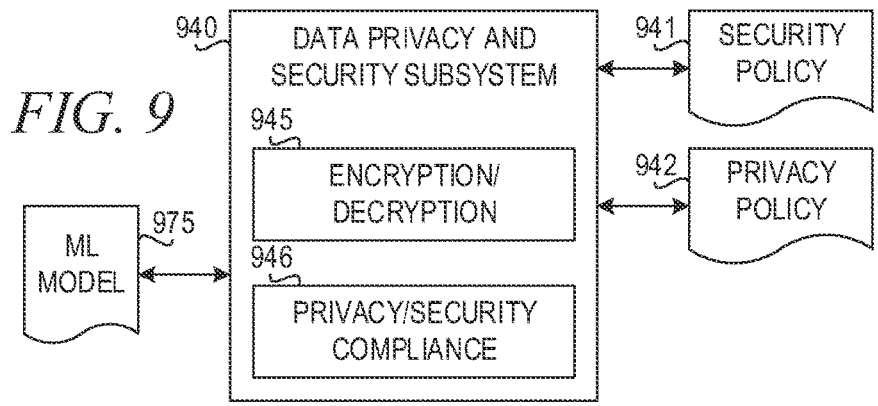
FIG. 9
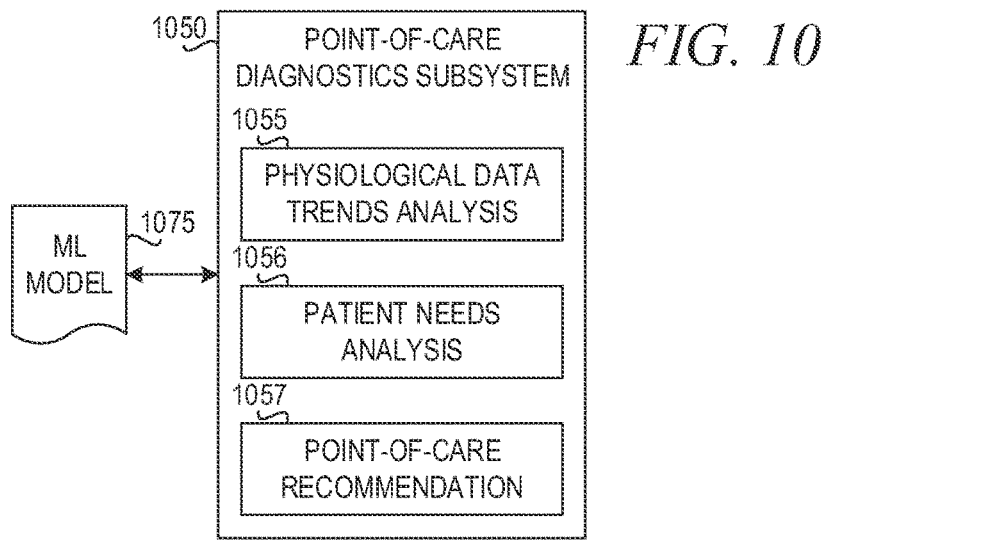
FIG. 10
FIG. 11
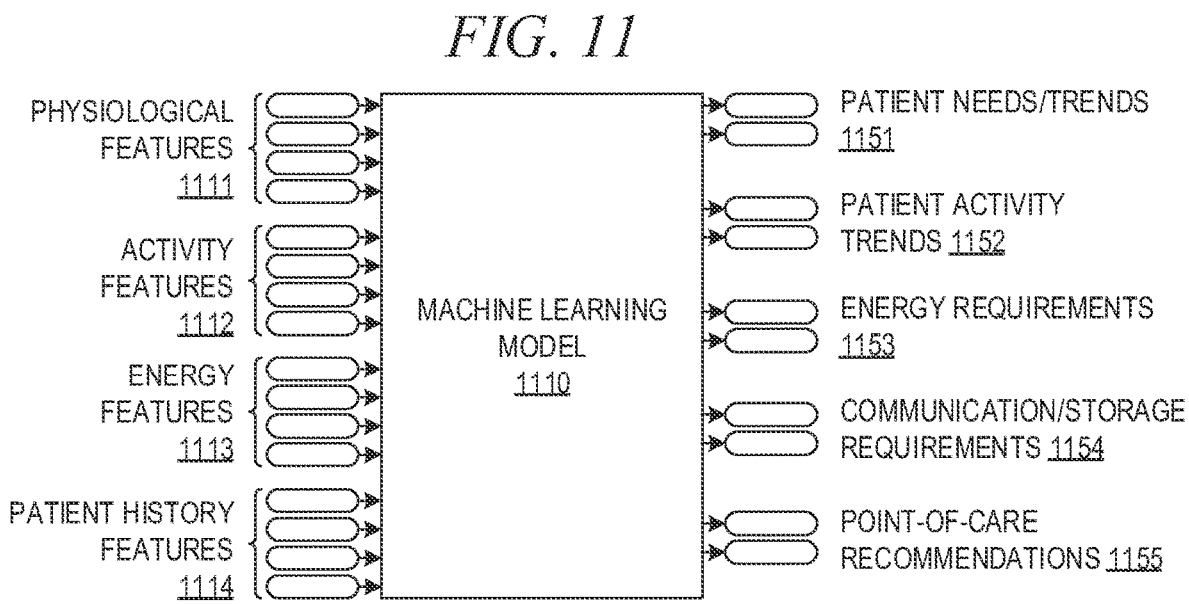

MULTI-SENSOR PLATFORM FOR HEALTH MONITORING

BACKGROUND

The present application relates generally to an improved data processing apparatus and method and more specifically to a multi-sensor platform for health monitoring.

Current wellness visits for annual checkup do not provide adequate detection and monitoring for health. Current healthcare sensors often lack precision, coordination from multiple sensors (non-invasive (non-wearable), wearable, and/or implanted health-sensors) with a lack of information related to personal tracking for daily activities, physiological data streams, cognitive information, environment, and behavior. Current healthcare sensor use of non-invasive monitoring is improving but may lack specific data metrics and patient context/trending for tracking specific health signals from physiological/cognitive data at a level needed to provide personalized health insights and care.

In addition, often data from multiple sensors are not coordinated against daily routines with proper understanding of patient activities and often wearable sensors are not high precision with continuous data stream, power support, low-cost, and used by patients in an automated manor that would permit ease of use, automated data transfer, automated power recharge, use of reusable sensors and disposable sensors that permit data stream personalization, tracking, insights, and care in their daily routines, at home, work, and in other environments.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to configure the processor to implement a multi-sensor health monitoring platform. The method comprises applying a machine learning model to predict patient needs and patient activity trends based on physiological features and activity features of the patient. The method further comprises applying the machine learning model to predict energy requirements for a plurality of medical sensors based on the predicted patient needs and patient activity trends. The method further comprises scheduling recharging of the plurality of medical sensors based on the predicted energy requirements and identifying one or more sensors from the plurality of medical sensors to set to an activate state based on the predicted patient needs and patient activity trends. The method further comprises collecting sensor data from the one or more sensors and applying the machine learning model to generate a point-of-care recommendation based on the collected sensor data.

In other illustrative embodiments, a computer program product comprising a computer useable or readable medium having a computer readable program is provided. The computer readable program, when executed on a computing device, causes the computing device to perform various ones of, and combinations of, the operations outlined above regarding the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above regarding the method illustrative embodiment.

These and other features and advantages of the present invention will be described in or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 9 is a block diagram illustrating a data privacy and security subsystem in accordance with an illustrative embodiment;

FIG. 10 is a block diagram of a point-of-care diagnostic subsystem in accordance with an illustrative embodiment;

FIG. 11 is a diagram illustrating a machine learning model for multi-sensor health monitoring in accordance with an illustrative embodiment.

DETAILED DESCRIPTION

Figure 1:
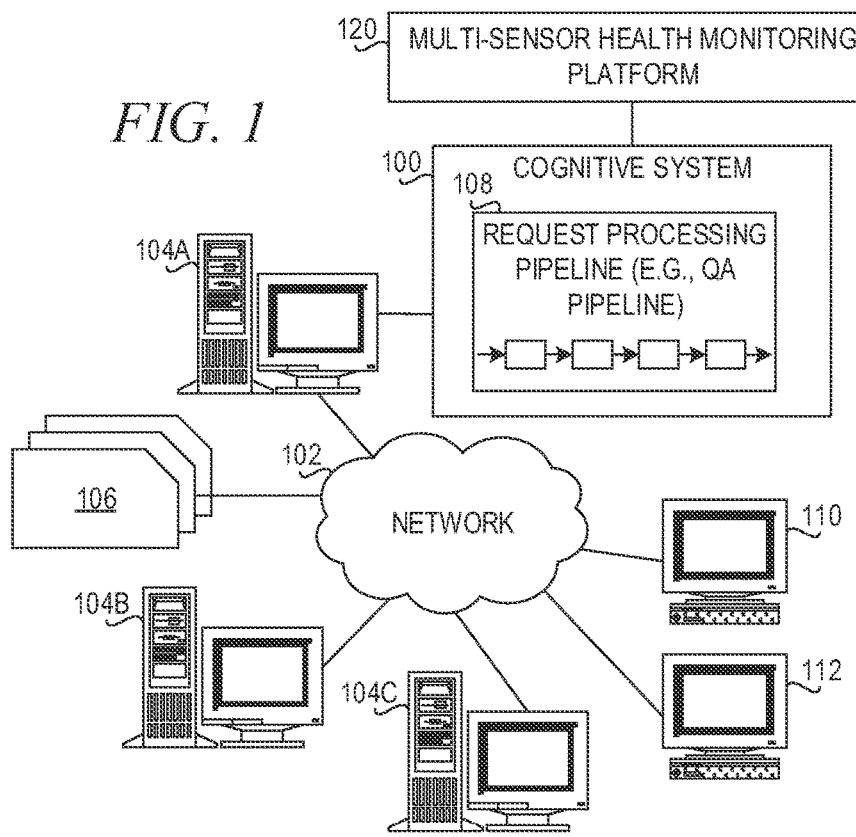
FIG. 1 depicts a schematic diagram of one illustrative embodiment of a cognitive healthcare system in a computer network.

The current health monitoring non-invasive (non-wearable) and wearable sensor paradigm has limited or periodic measurements at a clinic or doctor's office and may have limited home health sensor data. The current paradigm is reactive to data that are the out-of-normal range or due to illness. A patient goes to the doctor, clinic, or hospital for baseline health sensor data, such as wellness check blood pressure, weight, blood diagnostics test or urine diagnostics test. Alternatively, a patient has a sickness or accident and goes to the hospital, doctor, or emergency room for care. Patient data are discussed with a doctor or nurse and actions are taken if the data are outside the normal range. The patient receives direction for sickness and medication and follow-up visit if needed.

Current health non-invasive and wearable sensor monitoring is not well coordinated for personalized health monitoring with data privacy and security controls and multi-sensor management for personalized insights, care, and prediction. For these reasons, current health wearable sensors lack wide use and adoption. There is a need for better personalized health monitoring, early detection, disease monitoring, medication dose efficacy, trending, prediction, insights, and care.

The illustrative embodiments provide a healthcare multi-sensor technology hardware and software platform that by example can utilize non-invasive (non-wearable), wearable sensors, and/or point-of-care diagnostics, such as in a patient's home, that can complement hospital and clinic testing, monitoring for health insights and care improvements that help patients' lives. The multi-sensor platform of the illustrative embodiments uses integrated cognitive computing using data from, non-invasive sensors, wearable sensors, and/or point-of-care diagnostics that are tailored for personal health monitoring to provide disease detection, monitoring, insights, and care recommendations.

The illustrative embodiments use automated power management, power recharge to sensors, communication devices, data storage devices, wearable or Internet-of-Things (IoT)/AI Edge computing devices, encryption/security devices, smart watch, or smart phone, other on-person power transportation devices that support power access and interlock. Each of these devices provides flexibility to support personal patient needs and flexibility over time with learning and patient care provider power intervention and priority selection options. The illustrative embodiments include power/energy availability monitoring and trending, power efficiencies and controls to meet personal prioritized needs against health risk (e.g., life threat emergency, alerts, data analytics, trending key information and actions).

The illustrative embodiments use multiple sensor and point-of-care diagnostics selection, data tracking rate, algorithms with machine learning and classification against activities of daily living and personal needs with examples, such as but not limited to, early disease detection, chronic disease monitoring and elder patient monitoring for insights, care, intervention, and quality of life enhancements. The multi-sensor platform of the illustrative embodiments provides data streams awareness of patient risks, physiological data, environment, cognitive state, and patient behavior. The multi-sensor platform uses data from sensors, time stamped and tagged, to provide cognitive computing analysis, key data metrics tracking against specific patient chronic disease (s) and risk factors with machine learning, readout to patient, care provider with trending, insights, prediction for diseases, activities of daily living, medication efficacy, and opportunities to reduce risks (e.g., diet, exercise, sleep quality enhancements, physiological and/or cognitive targets), recommendation of doctor visits or alternate actions.

The health monitoring and wearable paradigm of the illustrative embodiments has precision home sensors for regular or continuous health contextual monitoring. The multi-sensor platform of the illustrative embodiments has automation of multiple sensors targeted to patient needs with home sensors and diagnostic data to complement clinic or other diagnostic data. The platform has cognitive or artificial intelligence (AI) learning and trending to predict and guide health professionals for patient care. The platform has low-cost, reusable, and disposable sensors and diagnostic with security, personal privacy, and options for patient personalization, power management, frequency of measurements, and gives patient trending and recommendations based on personal care. A patient uses automated sensors and diagnostics at home for baseline health sensor data, such as wellness check for blood pressure, weight, home blood diagnostics test or urine diagnostics test, which can be tailored for a patient's needs and compliment periodic clinic visits for blood or urine testing. Similarly, cognitive diagnostics using speech diagnostics and other diagnostics testing can be applied as appropriate for patients personalized needs.

Before beginning the discussion of the various aspects of the illustrative embodiments and the improved computer operations performed by the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a", "at least one of", and "one or more of" regarding features and elements of the illustrative embodiments. It should be appreciated that these terms and phrases are intended to state that there is at least one of the feature or element present in the illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein regarding describing embodiments and features of the invention, is not intended to be limiting of any particular implementation for accomplishing and/or performing the actions, steps, processes, etc., attributable to and/or performed by the engine. An engine may be, but is not limited to, software, artificial intelligence training, inference, and/or data analytics, hardware and/or firmware or any combination thereof that performs the specified functions including, but not limited to, any use of a general and/or specialized processor in combination with appropriate software loaded or stored in a machine-readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through one or more fiber-optic cables), or electrical signals transmitted through one or more wires.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, AI/hybrid cloud computers, smart phones, and/or AI edge computers or servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), accelerators, application specific integrated circuits (ASIC), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
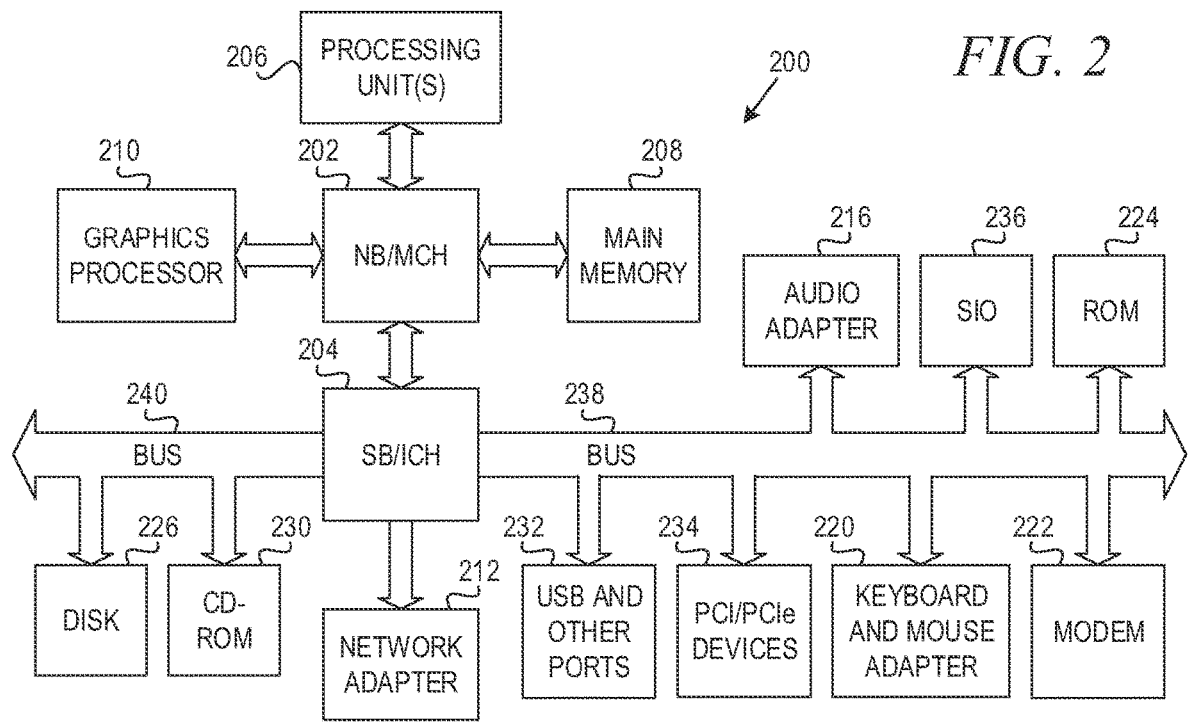
FIG. 2 is a block diagram of an example data processing system in which aspects of the illustrative embodiments are implemented.
Figure 3:
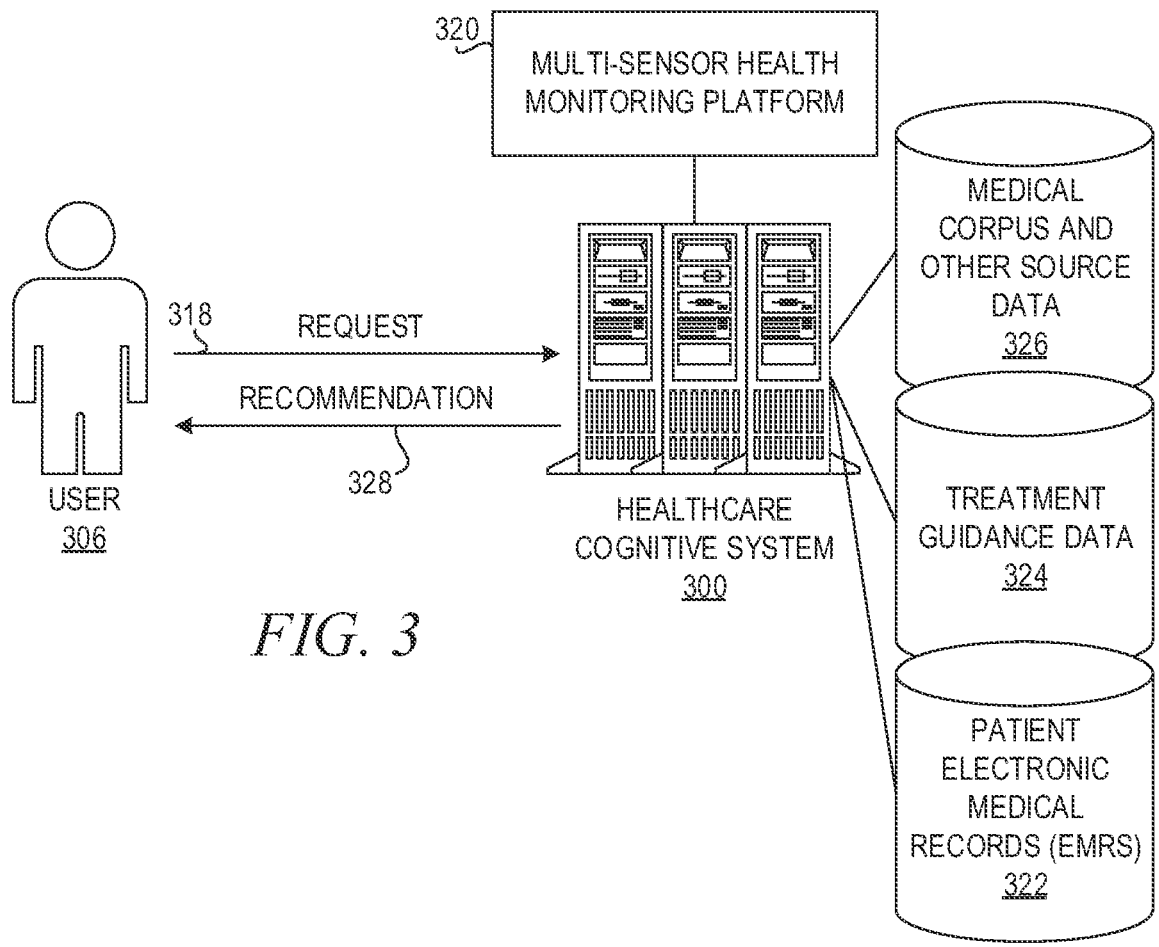
FIG. 3 is an example diagram illustrating an interaction of elements of a healthcare cognitive system in accordance with one illustrative embodiment.

As noted above, the present invention provides mechanisms for graphical presentation of relevant information from electronic medical records. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation regarding the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the healthcare application that is implemented in the cognitive system of the present invention is a healthcare application for presenting relevant information using a graphical presentation engine.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining, and evaluating final results generated by the processing performed by multiple request processing pipelines, and other control and interaction logic that facilitates the utilization of multiple request processing pipelines.

As will be discussed in greater detail hereafter, the illustrative embodiments may be integrated in, augment, and extend the functionality of these QA pipeline, or request processing pipeline, mechanisms of a healthcare cognitive system regarding an electronic medical record completeness and data quality assessment mechanism.

Thus, it is important to first establish how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

FIG. 1 depicts a schematic diagram of one illustrative embodiment of a cognitive system 100 implementing a request processing pipeline 108 in a computer network 102. The cognitive system 100 is implemented on one or more computing devices, smart phones, AI Edge computers or the like 104A-C (comprising one or more processors and one or more memories, and potentially any other computing device elements generally known in the art including buses, storage devices, communication interfaces, and the like) connected to the computer network 102. Computing devices 104A-C may comprise cloud computing or personal computers, such as one or more desktop computers, laptop computers, smart phones, etc. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like, and the answer may be returned in a natural language format maximized for efficient comprehension in a point-of-care clinical setting. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106.

In some illustrative embodiments, the cognitive system 100 may be the IBM Watson™ cognitive system available from International Business Machines Corporation of Armonk, New York, which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare-based operations. For example, depending upon the particular implementation, the healthcare-based operations may comprise patient diagnostics medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a multi-sensor health monitoring platform 120 to support at-home wearable sensors and point-of-care diagnostics that can complement hospital and clinic testing, monitoring for health insights and care improvements that help patients' lives.

Multi-sensor health monitoring platform 120 uses low-cost disposable or reusable sensors or diagnostics. These sensors may be on the body, such as an adhesive bandage-like sensor or the like. The sensors may include electrocardiogram (ECG) sensor, electromyogram (EMG) sensor, or photoplethysmogram (PPG) sensor, such as a fingernail sensor or wristwatch sensor, for example.

Multi-sensor health monitoring platform 120 may be an electronic multi-sensor hub that may be embodied within a smart phone or a device that can be carried in a purse or pocket or on a belt. The multi-sensor health monitoring platform 120 may have a power supply that may be part of a multi-sensor hub or may have a separate power supply, such as a battery in a belt, shoe, or purse, with smart power management. Multi-sensor health monitoring platform 120 may have an on-body or off-body integrated system to support monitoring power, recharging, data transmission, timing, etc. Charging or data communication may be wireless or wired or may be from on-body to on-body, off-body to on-body, or on-body to off-body. A HUB is a multi-port interconnection device that can be a computer that connects to multiple sensors and/or data storage devices.

Off-body automated charging or data communication may be wireless or wired and may include sources, such as an office chair or desk, car, bed, couch, purse, backpack, briefcase, or one or more combinations of power or data transfer and collection points.

Encrypted data may be transmitted to and from health professionals by wireless approved Food and Drug Administration (FDA) and Health Insurance Portability and Accountability Act (HIPAA) compliant input via smart phone, cloud, or other means. Personal patient data and sensitive data can alternatively be maintained locally in a secure computing device such as in a smart phone or AI/Edge Computing device to reduce exposure of patient data via communications and to be more energy efficient by driving data algorithms at or near the source of the data generation sensors with AI/training, inference, insights, and recommendations leveraging opportunity for external information and local/at-home data and computation at the AI/edge computing/home location. Multi-sensor health monitoring platform 120 follows recommendations, actions, and trending to manage wellness or disease.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide a cognitive summary of EMR data for patients. However, it should be appreciated that this is only an example implementation and other healthcare operations may be implemented in other embodiments of the healthcare cognitive system 300 without departing from the spirit and scope of the present invention. Other examples of healthcare cognitive system 300 can include a smart phone, a computer, an AI/edge computing device, cloud computing system, and/or combinations thereof. In one embodiment, healthcare cognitive system 300 may be a smart phone, computer, or AI edge computing device.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302, social history, and demographic information about the patient, symptoms, and other pertinent information obtained from responses to questions or information obtained from medical equipment used to monitor or gather data about the condition of the patient. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a cognitive summary of EMR data 328 to the user 306 to assist the user 306 in treating the patient based on their reported symptoms and other information gathered about the patient. The healthcare cognitive system 300 operates on the request 308 and patient attributes 318 utilizing information gathered from the medical corpus and other source data 326, treatment guidance data 324, and the patient EMRs 322 associated with the patient to generate cognitive summary 328. The cognitive summary 328 may be presented in a ranked ordering with associated supporting evidence, obtained from the patient attributes 318 and data sources 322-326, indicating the reasoning as to why portions of EMR data 322 are being provided.

Note that EMR data 322 or data presented to the user may come from home readings or measurements that the patient makes available and are collected into EMR data 322.

In accordance with the illustrative embodiments herein, the healthcare cognitive system 300 is augmented to include a multi-sensor health monitoring platform 320 to support at-home wearable sensors and point-of-care diagnostics that can complement hospital and clinic testing, monitoring for health insights and care improvements that help patients' lives. Multi-sensor health monitoring platform 320 provides automation of data collection frequency, power management of sensors and recharge, security, and encryption. Multi-sensor health monitoring platform 320 uses reusable and/or disposable sensors that meet personalized care of patient needs with data monitoring and calibration, data trending, algorithms and prediction to improve care of patients in need of wellness monitoring, disease monitoring, medication monitoring, outpatient or home monitoring, aging care, care facility monitoring to complement hospital or clinic care if and when needed.

Multi-sensor health monitoring platform 320 provides sensor power delivery from on-body power sources or off-body power sources due to monitoring and prediction of energy requirements of specific sensors, charge by near-field communication, wireless charging technology, energy scavenging technology, or other known charging technology.

In one embodiment, multi-sensor health monitoring platform 320 uses an on-body battery or energy source to charge, recharge, or remotely power sensors on the body. For example, an on-body battery may be embodied within a belt, shoe, hat, wrist or ankle, shirt, pants, socks, or other clothing. In an example embodiment, the on-body battery may provide power to on-body reusable or disposable adhesive bandage-like sensors. Multi-sensor health monitoring platform 320 may make use of wireless charging, such as near-field communication (NFC) or alternate wireless charging. The platform may use wireless or wired charging, such as a shirt, pants, socks, etc. with power transmission channels to leverage power transfer from a point of energy, such as a belt battery, to an area near a sensor, such as a chest or wrist, by means of an antenna near the point of energy or through a shirt or other garment to an antenna near the point of the sensor. In one embodiment, multi-sensor health monitoring platform 320 uses a higher voltage battery to transmit higher power to a sensor battery with on-sensor inductor/transformer to enhance sensor use time at lower use voltage. In one embodiment, multi-sensor health monitoring platform 320 uses one or more off-body energy delivery points to on-body sensors or on-body battery to support automated recharge based on circuit monitoring, energy consumption, and cognitive monitoring of sensor use times and energy level for patient needs. External energy sources may include a patient bed, a chair, car seat, wheelchair, crutches, cane, or alternate source.

Multi-sensor health monitoring platform 320 uses sensor communications or data transfer from one or more off-body electronics sources and/or off-body multi-electronics communication sources to one or more on-body electronic hubs/sensors and/or electronics management or transfer locations with appropriate controlled encryption, privacy, and security for patient needs and compliance requirements. Multi-sensor health monitoring platform 320 provides automation of data or communication of information to sensors and from sensors or edge computing or smart devices or home health electronics platforms. Multi-sensor health monitoring platform 320 uses cognitive computing and patient needs to provide maintenance of sensors, update monitoring of sensors from off state or idle mode to on state for measurement, data collection, monitoring, data analysis, algorithm and options to trend and store data. Multi-sensor health monitoring platform 320 may compute with local data or may transmit data to another location on body or off body, to use data from one or more sensors or diagnostics to provide insights, trending, and care to assist a patient and provide insights to care providers, predictions, recommendations for care, wellness monitoring, or actionable alarms or other actions to assist the patient.

Multi-sensor health monitoring platform 320 may use data management, storage, artificial intelligence, machine learning, and cognitive computing to provide care to the patient based on large data insights from other patients and/or personalized care to a specific patient based on the individual patient's needs, diseases, medications, and other digitally monitored information, physiological data trends from sensors, diagnostics and/or other relevant information to assist in caring for the patient.

Multi-sensor health monitoring platform 320 provides an on-body smart data hub and/or off-body smart data hub to collect, monitor, store, trend, predict, and communicate information about the patient to assist in healthcare monitoring, trending, prediction, and care. Multi-sensor health monitoring platform 320 may use wireless communication and data transfer management with cognitive management of key information for the patient and the ability to adjust and update the relevant sensing and diagnostic data and analysis over time. In one embodiment, multi-sensor health monitoring platform 320 uses one or more reusable sensors and diagnostic data input for the patient by periodic or continuous data streams according to patient needs from one or more sensors and diagnostic sources, including at-home sources, care sources, at-work sources, hospital and clinic data sources, or alternate data sources.

In one embodiment, multi-sensor health monitoring platform 320 uses one or more wired, wireless, or wired and wireless sources to provide data transfer from one or more sensors either with all data, post at sensor, or edge computational algorithms and data sorting or to one or more data hubs or smart electronic control points on body or off body. Multi-sensor health monitoring platform 320 may provide communications based on the patient's needs, sensors and diagnostics needed, frequency of data transfer needs, power versus data priorities as set forth based on patient needs, care provider guidance, or cognitive or AI learning over time for the patient and patient sensor/diagnostic needs and updated requirements over time. Multi-sensor health monitoring platform 320 may use reusable sensors or disposable sensors on different body locations outside the body, inside the body, or remote from the body. The multi-sensor health monitoring platform 320 may provide a battery or energy source to charge, recharge, or remotely power sensors on the body. Multi-sensor health monitoring platform 320 may use wireless data transfer, such as near-field communication (NFC) or other similar wireless data transfer.

In one embodiment, multi-sensor health monitoring platform 320 uses wireless and wired data transfer, such as use of a shirt with data transmission channels to leverage data transfer from point of electronic sensor or hub, such as belt electronics, to other body area, such as an area near a sensor, such as a chest or wrist by means of NFC. Multi-sensor health monitoring platform 320 may provide an antenna near the point of an electronics hub or sensor, such as an electronic belt or pocket device and through a shirt, pants, or socks with electronic communication channels. Data communication may comprise a combination of wired and wireless communication to sensors at the chest, wrist, ankle, or foot. Multi-sensor health monitoring platform 320 may use clothing with electronics that support data communication and power transfer. Multi-sensor health monitoring platform 320 may use one or more off-body electronic smart hubs or data management points that support data transfer from in or on body and/or off body sensors to support patient monitoring. Examples of data transfer hubs may include a patient bed, chair, car seat, wheelchair, crutches, cane, or other similar devices.

In another embodiment, multi-sensor health monitoring platform 320 uses micro-controllers, electronic, optical, or other physiological sensors or diagnostics. Sensors may contain memory storage devices, batteries, energy scavenging components, and other components. The sensors may be small, low-cost, reusable, or disposable. For example, sensors may provide secure communication with encryption, optical communication technology, radio frequency (RF) communication using an antenna, etc. Sensors may provide data history, data add/transfer time, etc. Sensors may also be HIPAA compliant. Furthermore, sensors may contain a microprocessor, non-volatile (NV) storage, field programmable gate arrays (FPGA), etc. Sensors may be small form factor. Sensors may be from a standard platform or may be custom. Still further, the sensors may contain a micro-battery or capacitors, energy scavenging capability, NFC recharge, power management/efficiency, or solid-state or polymer batteries. In addition, sensors may have integrated nano- or micro-sensors, integrated microsystems, application form factor, bio and environmentally compatibility, sealing technology (use of liquid crystal polymer or alternate material such as Ti can).

In one embodiment, multi-sensor health monitoring platform 320 uses one or more types of sensor, such as electroencephalogram (EEG), electrocardiogram (EKG), electromyogram (EMG), temperature sensors, force sensors, inertial measurement unit (IMU) sensors, photoplethysmogram (PPG) sensors, blood pressure sensors, biomarker sensors, glucose monitoring sensors, pulse rate, heart rate, etc. as physiological sensors, each with an opportunity to link to time stamp for data and reference of data to context of a patient, such as at rest (sleeping, sitting) or active in sports, walking, running, or other activities, as well as link to patient medications, age, or other relevant patient care information, family history, genomic data, etc. Multi-sensor health monitoring platform 320 may use reusable sensors or disposable sensors, sensor subsystems, or sub-components, etc.

In one embodiment, multi-sensor health monitoring platform 320 uses electronics to manage power consumption by means of automated monitoring battery or energy source power level, rate of use. Additionally, multi-sensor health monitoring platform 320 supports automated recharge. Multi-sensor health monitoring platform 320 prioritizes sensors or electronics for power consumption, turns components off or to a sleep state or turns components on or in a wake state based on the prioritization. These components may include sensors, electronics, storage devices, communication devices, or the like. Multi-sensor health monitoring platform 320 may select local or remote data storage. Multi-sensor health monitoring platform 320 may schedule a time and frequency of data transfer. Multi-sensor health monitoring platform 320 may select data transfer from local power or external power, such as NFC, use of one or more power supplies, such as one or more batteries, or energy harvesting. Multi-sensor health monitoring platform 320 may select a recharge rate and time based on smart trending for power and data management. Multi-sensor health monitoring platform 320 may employ encryption on personal or health professional targeted data streams based on personal needs and data from different sensors where specific one or more sensors may have higher priority for critical data than other sensors and, therefore, may have a particular priority for sensing, data collection, analysis, and communications.

In another embodiment, multi-sensor health monitoring platform 320 uses specific sensors with unique identifiers and tags and patient unique identifiers and tags with privacy, security, and encryption. Multi-sensor health monitoring platform 320 may provide controls to patient or health providers or authorized persons for electronic health records management, reference, and storage, including cloud accounts. Multi-sensor health monitoring platform 320 may use sensor tags and location data based on patient body location and the function of the sensor(s) to provide multiple streams of data to assist patient care. Multi-sensor health monitoring platform 320 uses large data, patient reference, trending data, and machine learning algorithms to assist in patient care.

In one embodiment, multi-sensor health monitoring platform 320 may be used for infants, healthy patients, injured patients, diseased patients, aged patients, or other patients for medical tracking and health and wellness monitoring and intervention, for rehabilitation, sports, or other patient benefits, for health payers, for healthcare providers, and for other purposes. The multi-sensor health monitoring platform 320 of the illustrative embodiments may be applied to robotics, transportation, bridges or infrastructure, or other purposes of monitoring and maintenance. Multi-sensor health monitoring platform 320 may be used for reliability and precision monitoring of hardware, cognitive learning, and recommendations. Multi-sensor health monitoring platform 320 may be used for training and safety or ergonomic benefits. Alternatively, multi-sensor health monitoring platform 320 may be used for pets and animal monitoring.

Non-invasive (non-wearable) and wearable sensors are selected based on precision of data from the health sensors/diagnostics tests, ability to correlate the type of physiological data (examples include cognitive data, pulse rate, blood pressure, blood diagnostics, and/or urine analysis), cognitive assessment, such as with speech analysis. Each sensor or diagnostic data may be recorded with both a time stamp and a timeline relative to when the data is taken from the patient relative to the patent's environment (activity level, sleeping, awake, active, at rest, exercising, etc.). The illustrative embodiments provide data algorithms/trending, such as against "activities of daily living" (schedule/routine) of the patient and establish physiological data sets that are normal during sleep, awake periods of activity such as office work, periods of normal/low stress, periods of high stress, periods of exercise or higher exertion, timing relative to medications if treating a disease and the effectiveness/efficacy of the medication doses and impact on the patients reaction to the medications (i.e., Parkinson Disease (movement, tremors, on/off medication state) and based on these data algorithmic training and inference assessments, lead to insights, risks, recommendations, and adjustments to the patient's care to improve/reduce health risks, adjust medication doses, or timing to aid the patient through life. Examples can be related to patient needs. Example 1 can include patient natural aging and cognitive decline where cognitive speech diagnostic can be evaluated one or more times per day, week, or month along with time of day and patient routine and activities adjusted to aid the patient with brain stimulation or medications based on patient needs, activity level, independence, or care facility. Example 2 could be applicable to a patient who has Parkinson disease where monitoring of disease progression, medication efficacy, impact on mobility, tremors, or cognitive state could leverage sensors such as monitoring sit-to-stand, walk, movements, etc. as well as the medication dose levels, timing of medications and on/off state of effectiveness of those medications and adjustments in medications as given by the healthcare provider using artificial intelligence leveraging other patients with Parkinson Disease, this patient's unique physiological data, trends, activities of daily living and sensor data and disease progression over time to provide the best outcomes possible to improve the patent's quality of life. Example 3 can leverage use of non-invasive sensors, wearable sensors, speech diagnostics, point-of-care blood diagnostic tests, urine tests and/or implanted sensors to guide patient monitoring relative to activities of daily living, to help determine the best sensors, frequency of sensor data for monitoring, AI algorithm for data analysis and enhancements, training and inference for personalized patient care needs while also providing automated power recharge of sensors as needed based on voltage monitor sensors within the physiological sensors, time of sensors operation and data transmission, etc.

Figure 4:
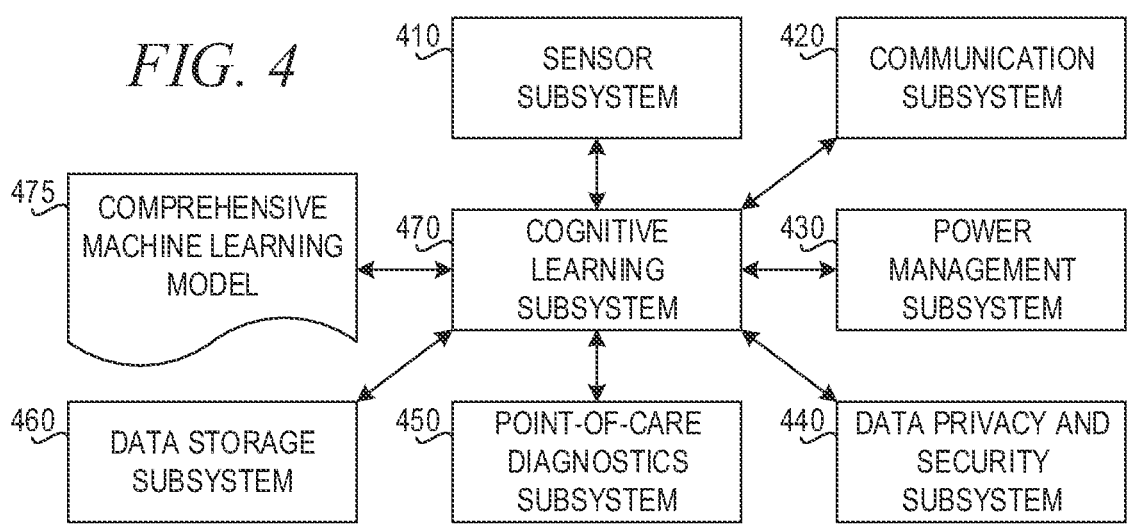
FIG. 4 is a block diagram of a multi-sensor health monitoring platform in accordance with an illustrative embodiment.

FIG. 4 is a block diagram of a multi-sensor health monitoring platform in accordance with an illustrative embodiment. The multi-sensor health monitoring platform (such as but not limited to a smart phone, computer, laptop, cloud computer, edge computing device or the like) comprises a cognitive learning subsystem 470 connected to a sensor subsystem or HUB 410, communication subsystem 420 (such as a smart phone, smart watch, computer, or alternative device), power management subsystem 430, data privacy and security subsystem 440, point-of-care diagnostics subsystem 450, and data storage subsystem 460. Cognitive learning subsystem 470 generates and uses comprehensive machine learning model 475.

The effectiveness of using one base machine learning model could be applied for patient personalized healthcare with adjustments made to fit the patient needs and would be superior to the typical monitoring being used today. Over time, there are adjustments that would be developed based on many different categories of health state, wellness, disease, age, family history, etc. Use of large data analysis from large populations with physiological data points and streams of data over time, relative to the patient's activities of daily living (e.g., normal data patterns during rest, awake with minimal activity, exercise/high activity periods, age, fitness and cognitive activities, wellness/disease state and relative progression, medication efficacy/change over time) when compared to large sets of data for other humans with similar health records, family history and trends. Assume the patient's personalized health tracking, monitoring, training, and inference/insights across many categories of patient needs, wellness, disease, aging, will continue to improve in time as above practices would become more widely used/adopted in the industry, and likely more advanced algorithms and machine learning could be applied over time to targeted healthcare needs for monitoring and quality of life enhancements.

In accordance with the illustrative embodiment, the subsystems operate as a comprehensive system. For example, the sensor subsystem 410 activates and deactivates sensors based on patient needs determined by point-of-care diagnostics subsystem 450 and based on available power, as determined by power management subsystem 430. As another example, communication subsystem 420 communicates and encrypts sensor data to be transmitted to a healthcare provider based on compliance with security and privacy policies, as controlled by data privacy and security subsystem 440.

The multi-sensor health monitoring platform learns data trends, patient needs, power trends and needs, etc. via cognitive learning subsystem 470 and comprehensive machine learning model 475. In one embodiment, cognitive learning subsystem 470 learns data trends from sensor subsystem 410, communication trends from communication subsystem 420, power availability trends from power management subsystem 430, and storage trends from data storage subsystem 460. In another embodiment, cognitive learning subsystem 470 also predicts which sensors will be needed at different times of day based on patient activity trends, as determined based on sensors at sensor subsystem 410, and based on the health needs of the patient, as determined by point-of-care diagnostics subsystem 450. In another embodiment, cognitive learning subsystem 470 predicts the best time or frequency to communicate sensor data via communication subsystem 420 or the best time or frequency to store sensor data via data storage subsystem 460. Cognitive learning subsystem 470 also predicts power availability based on power availability trends and patient activity trends, as determined based on sensors at sensor subsystem 410. Based on the prediction of which sensors will be needed at different times of day and the predicted power availability, power management subsystem 430 charges an on-body battery or one or more sensors.

In addition to examples described above, another example would be for use of precision sensors and diagnostics to aid patients undergoing cancer treatment. For instance, for cancer patients who would be undergoing chemotherapy and visits to hospital or testing facility to undergo blood test and/or urine analysis to track ongoing trends for a person's key metrics associated specific cancer, immunity, risk factors, recovery rate, etc., could obtain an increased number of tests with a simple urine analysis or blood test at home daily to compliment visits to hospital or test facility and have increased accuracy, trending, algorithms, and insights. These would use daily or with increased frequency of testing relative to hospital or test facility that might be two to six weeks timing between diagnostics blood and/or urine analysis while providing the patient and patient medical treatment team improved health insights, much lower cost (such as ten times lower cost, for example), reduced risk of exposure while with reduced immunity/white blood cell count from other health risk exposures and less inconvenience of travel to and from hospital or diagnostic test facility.

Figure 5:
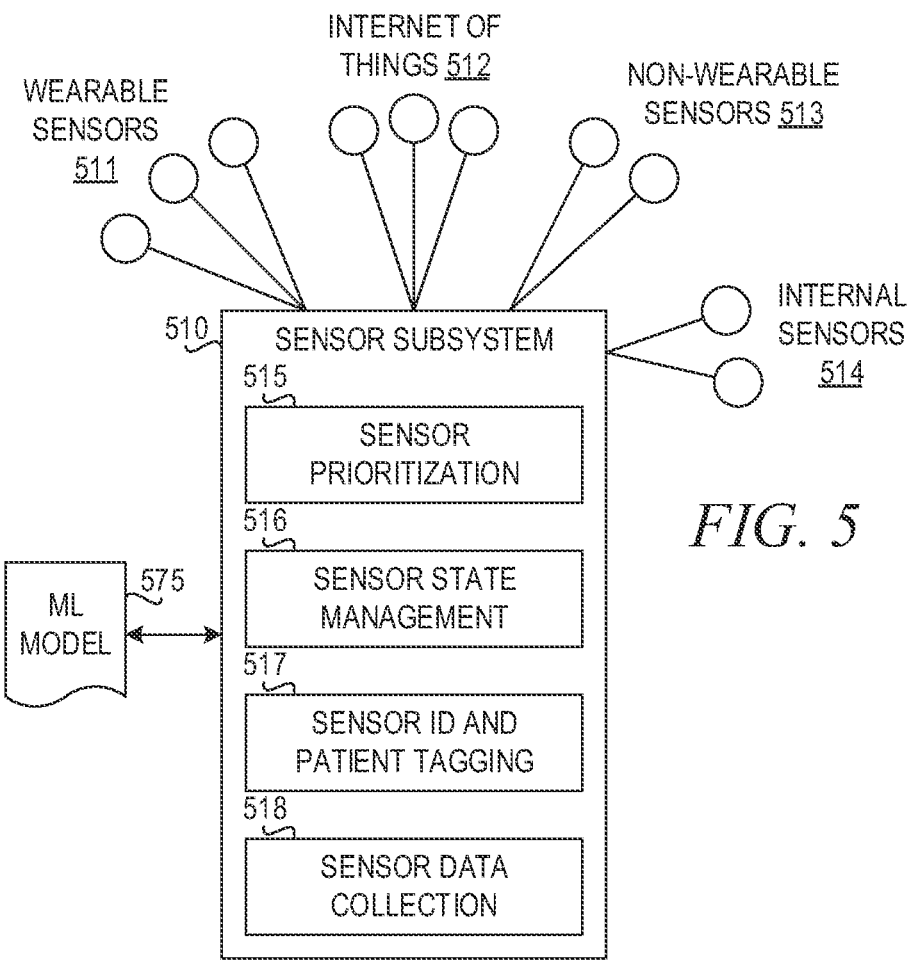
FIG. 5 is a block diagram of a sensor subsystem in accordance with an illustrative embodiment.

FIG. 5 is a block diagram of a sensor subsystem in accordance with an illustrative embodiment. Sensor subsystem 510 is connected to wearable sensors 511, Internet of Things (IoT) sensors 512, non-wearable sensors 513, and internal sensors 514. Wearable sensors 511 may comprise heart rate monitors, blood glucose monitors, and the like. IoT sensors 512 may comprise fitness bands, pedometers, smart scales, and the like. Wearable sensors 511 may also comprise adhesive bandage-like sensors, for example. Non-wearable sensors 513 may include blood diagnostics or urine analysis. Internal sensors 514 may comprise blood pressure monitor or heart pulse monitor.

Sensor subsystem 510 comprises sensor prioritization component 515, sensor state management component 516, sensor identifier (ID) and patient tagging component 517, and sensor data collection component 518. Sensor prioritization component 515 determines a priority of the sensors 511-514 based on the patient's activities and health needs. For example, at certain times of day, such as before and after eating, a patient may need a blood glucose reading. Sensor prioritization component 515 determines which sensors have priority for being in an active state to be provided power or for recharging. Sensor state management component 516 sets the active or inactive state of each sensor 511-514. For example, when a given sensor is not being used and does not need to be recharged, sensor state management component 516 sets the states of the given sensor to a sleep state or inactive state.

Sensor ID and patient tagging component 517 provides a sensor identifier and patient tag for sensor data based on the sensor type and location on the patient's body. For example, sensor ID and patient tagging component 517 may provide a unique identifier for a heart rate monitor attached to the patient's wrist and provide location information identifying the patient's wrist. Sensor ID and patient tagging component 517 also provides a patient tag to identify the patient as well as time and date information. Sensor data collection component 518 collects the sensor data with IDs and patient tags for communication and/or storage. Sensor data collection component 518 collects multiple streams of sensor data for the various sensors 511-514.

Sensor subsystem 510 uses machine learning model 575 to perform the operations of prioritizing sensors, setting sensor states, and collecting the sensor data. Sensor subsystem 510 can use machine learning from a larger patient data base and learning, such as may be available from a hybrid cloud data center, which could check for patients having "potential health related conditions," wellness, age range, specific diseases, genetics/DNA, medications, activity level, age, activity level, culture, risks, etc. to draw from. These larger data sets could be streamlined through algorithms, standard range limits associated with patient context/activities of daily living for at rest/sleeping, awake low level activity, high activity level, time of day and measurement tracking to focus on longer term day-to-day, week-to-week, month-to-month, year-to-year trends beyond patient-specific trends relative to like humans. The artificial intelligence training can be established using a cloud computing system, or smaller versions can be run locally at home using AI/edge computer/smart phone, etc. to take the specific patient larger data-sets, identify trends, data rates, data rate adjustments, or risk factors, and to provide inference/insights for the patent and their healthcare professional team/other family members such as emergency alert, to trend awareness and risk factors based on the specific patients medical issues.

Input Information:

First input information inputs may include large data set from the cloud or other data base, training and inference— insights recommendations and outcomes relative to time and patient similarities. Second input information and data inputs may be from the targeted patient personalized health sensors and sensor data targeted to support the patient's personal health management needs. Third input information and data may be on patient health records and care provider recommendations/medications, etc., patient history, prior patient sensor and diagnostic data taken at home, at hospitals, at medical test facilities, etc. Algorithms, training and inference from the platform may review episodic and streaming data to assess those data within targeted patient acceptable ranges relative to patient environment/context (sleep time, awake, rest, high activity, etc.).

Output Information, Data, Insights, and Recommendations:

First output from data analysis, classification if within target safe range for patient or outside safe data range being too high or too low, training/learning from history of the patient and reference to large data set to understand risks and actions that may be appropriate based on the classification and inference or insights of what is likely or probable with probability estimates. This information pending type of risk and importance to notify patient, family, or healthcare providers. This information may indicate if there is an emergency or if no action is needed for acceptable key data, classification, and insights or actions. Second output may provide insights and recommendations from the sensors, hardware/computation and software with artificial intelligence assessments, such as examples of frequency of key sensor data outside normal ranges, timing level of one or more critical health sensor data, or combinations of multiple sensors outside normal range targets that might suggest a visit to a doctor or healthcare professional if needed, a validation sensor or diagnostic data readings or other actions based on personal health data relative to risk for that individual based on the health parameters being monitored and relative to large populations of like patients reference data, trends and outcomes so as to benefit the patient. Insights and recommendations may include (1) a visit to a doctor for a checkup on health, (2) a visit to a doctor for possible medication adjustment, (3) an emergency condition and recommendation that patient call emergency services or be taken by ambulance to a hospital, (4) nonemergency and no need to see a doctor but rather to continue monitoring key sensor data in days, weeks, months, or years to verify whether data stay within target patient range or whether data go outside targeted range to see a healthcare professional.

Figure 6:
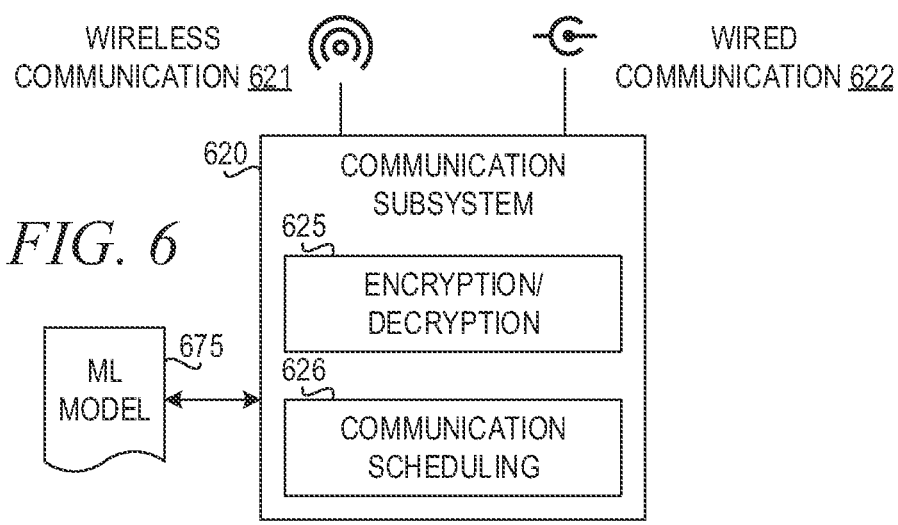
FIG. 6 is a block diagram of a communication subsystem in accordance with an illustrative embodiment.

FIG. 6 is a block diagram of a communication subsystem in accordance with an illustrative embodiment. Communication subsystem 620 uses wireless communication 621 and wired communication 622. Wireless communication 621 may include any known wireless communication technology, such as Near-Field Communication (NFC). Wired communication 622 may include Ethernet, Universal Serial Bus (USB), or the like.

Communication subsystem 620 comprises encryption/decryption component 625 and communication scheduling component 626. Encryption/decryption component 625 applies encryption being stored or transmitted to protect the security of sensor data and applies decryption of patient data being received or retrieved from storage. In one embodiment, encryption/decryption component 625 applies encryption/decryption based on privacy and security policies, as determined by data privacy and security subsystem 440 in FIG. 4.

Communication scheduling subsystem 626 schedules communication of sensor data based on data trends, patient health needs, and patterns of activity of the patient. For example, communication scheduling subsystem 626 may schedule communication of sensor data based on when the sensors take critical measurements, when the patient is at rest, when communication subsystem 620 has a good connection using wireless communication 621 or wired communication 622, etc. Communication scheduling subsystem 626 may determine the best time or frequency of communication using machine learning model 627.

Communication scheduling system 626 may use machine learning to determine if data is normal, outside targeted safe range, or suspect/defective reading based on sensor data, specifications, personal health sensor plan etc. For example, suspect data in acceptable range may indicate patient is well and data readings are normal; however, if patient data is outside normal range, this may indicate patient has a health risk. Based on risk level and predicted timing of risk event, communication scheduling system 626 may determine if an emergency call for help or ambulance is warranted, if action should be taken for a future doctor or healthcare visit, or if a recommendation should be made to healthcare provider for adjustment of medicine or other recommendations. Alternatively, if data are outside normal range, this result and analysis may be due to a false sensor reading and indicate that the sensor is defective, low on power, or needs replacement pending other indications and sensor information.

Figure 7:
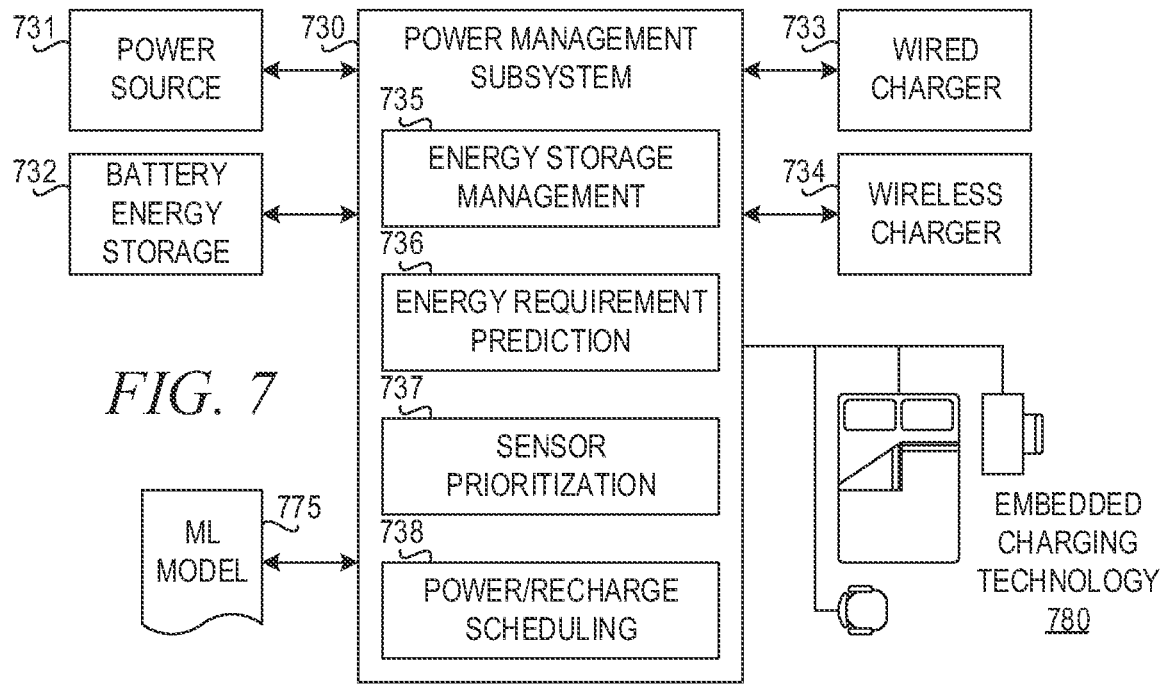
FIG. 7 is a block diagram of a power management subsystem in accordance with an illustrative embodiment.

FIG. 7 is a block diagram of a power management subsystem in accordance with an illustrative embodiment. Power management subsystem 730 manages power source 731, batter energy storage 732, wired charger 733, and wireless charger 734. Power source 731 may be a persistent power supply, such as an alternate current (AC) power supply or a transformer that converts AC power to direct current (DC). Battery energy storage 732 may be a rechargeable battery, such as a lithium-ion battery. Battery energy storage 732 may be embodied within the multi-sensor health monitoring platform, carried in a pocket or purse, or attached to the patient's body, such as in a belt, shoe, hat, or the like.

Wired charger 733 may be a Universal Serial Bus (USB) charging circuitry or a custom charging connector, for example. Wireless charger 734 may use inductive charging, such as the Qi wireless power transfer, or may use resonant inductive coupling, which achieves charging over greater distances. In one embodiment, a wireless charging inductive coil may double as an antenna for wireless communication, such as Near-Field Communication (NFC). Power management subsystem also manages embedded charging technology 780, which is embedded into objects in the patient's environment, such as a bed, office chair, desk, steering wheel, and the like.

Typically, near field communication and charging are utilized within distances of a few millimeters up to ten to twenty centimeters for efficiency. The illustrative embodiments may also use near field data transfer, energy monitoring, and recharging for many wearable sensors and implanted sensors. In addition, even though less power efficient, use of larger antenna and larger power supplies can also be leveraged where NFC does not meet the recharge requirements for some patients or to compliment NFC with recharge for low battery or needed data transfer, such as data metrics outside normal ranges against the patent environment/context that warrants more immediate data analysis, compilation, trending, insights, or recommendations to benefit the safety and well-being of the patient. Use of larger antenna and larger power supplies can support recharge and data transfer at distance from 10 to 20 cm to 60 cm, and even up to 200 cm (from under 2.5 feet to 10 feet where efficiency drops off dramatically at the much longer distances).

Power management subsystem 730 comprises energy storage management component 735, energy requirement prediction component 736, sensor prioritization component 737, and power/recharge scheduling component 738. Energy storage management component 735 determines trends in battery energy storage 732 and manages use of battery energy storage and recharging of battery energy storage 732 via power source 731. Energy storage management 735 may schedule recharge of battery energy storage 732 using machine learning model 775.

Energy requirement prediction component 736 uses machine learning model 775 to predict the amount of energy needed by various components of the multi-sensor health monitoring platform, including electronics, sensors, communication devices, storage devices, etc. Power management subsystem 730 then ensures battery energy storage 732 has enough energy to meet the demands of the various components, particularly the sensors.

Sensor prioritization component 737 prioritizes sensors for power and recharging based on the predicted energy needs of the sensors, the patient's health needs, and trends in patient activity. Power/recharge scheduling component 738 then schedules power delivery to sensors and other components based on the prioritization determined by sensor prioritization component 737. Power/recharge scheduling component 738 may schedule power delivery by wired charger 733 or wireless charger 734. Power may be delivered to sensors or other components for operation of the components or for charging. Sensors may have their own battery to be charged.

Figure 8:
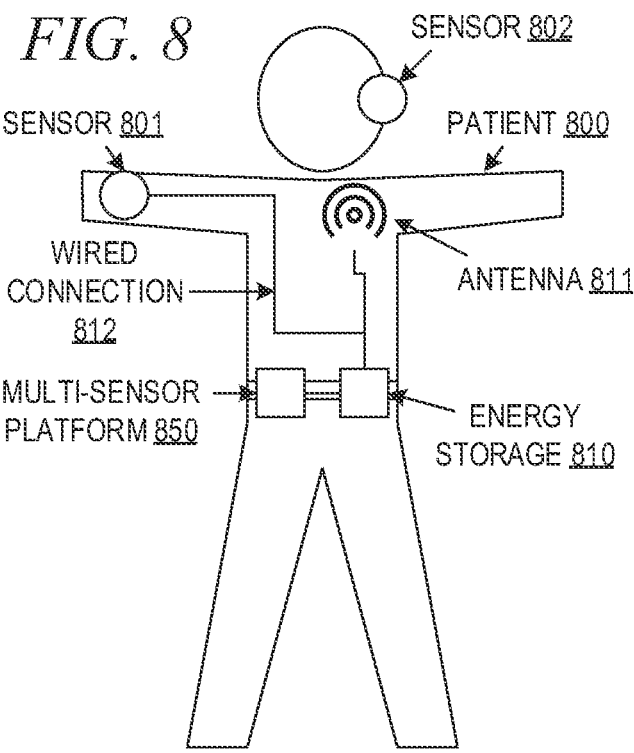
FIG. 8 illustrates an on-body power and communication channel delivery system in accordance with an illustrative embodiment.

FIG. 8 illustrates an on-body power and communication channel delivery system in accordance with an illustrative embodiment. Patient 800 wears multiple sensors 801, 802. Patient 800 also wears multi-sensor platform 850 and energy storage 810. In the depicted example, patient 800 wears multi-sensor platform 850 and energy storage 810 on a belt.

In accordance with the illustrative embodiment, patient 800 is wearing a garment, such as a shirt in this example, that provides a wired connection 812, which provides power and/or a communication channel to sensors 801, 802. Wired connection 812 may be a wire or embedded conductor in a shirt or other garment. Wired connection 812 may provide power from energy storage 810 to sensor 801. In one example embodiment, wired connection 812 provides power and/or communication to antenna 811. Sensor 802 communicates with antenna 811 to receive power from energy storage 810 or to communicate sensor data to multi-sensor platform 850.

FIG. 9 is a block diagram illustrating a data privacy and security subsystem in accordance with an illustrative embodiment. Data privacy and security subsystem 940 comprises encryption/decryption component 945 and privacy/security compliance component 946. Data privacy and security subsystem receives as input security policy 941 and privacy policy 942. Security policy 941 provides rules for providing secure communication and storage of patient data, including sensor data. Privacy policy 942 provides rules for protecting the privacy of the patient. In one embodiment, privacy policy 942 is based on laws, such as the Health Insurance Portability and Accountability Act (HIPAA). Data privacy and security subsystem 940 encrypts and decrypts patient data, including sensor data, being transmitted and stored based on security policy 941. Privacy/security component 946 determines which patient data or sensor data should be communicated or stored based on privacy policy 942.

Data privacy and security can be managed with data encryption in collection, transmission and analysis, secure hardware/software, and independent and verified passcodes. As a further precaution, personal data can be kept local using AI/edge computing with appropriate data storage security and only data analysis, results, trends, and insights sent to the patient and healthcare professionals using proper encryption and independent and verified passcodes. Machine learning may be applied for data privacy and security by means of using personal security data, such as fingerprints, eye retina scan, or other human unique identifiers for added security in addition to encryption and verified passcodes.

FIG. 10 is a block diagram of a point-of-care diagnostic subsystem in accordance with an illustrative embodiment. Point-of-care diagnostic subsystem 1050 comprises physiological data trends analysis component 1055, patient needs analysis 1056, and point-of-care recommendation component 1057. Physiological data trends analysis component 1055 identifies trends in sensor data and patient activity using machine learning model 1075. Patient needs analysis component 1056 determines and predicts patient needs based on sensor data and other patient data, such as an electronic medical record (EMR), using machine learning model 1075. Point-of-care recommendation component 1057 generates patient recommendations using machine learning model 1075.

FIG. 11 is a diagram illustrating a machine learning model for multi-sensor health monitoring in accordance with an illustrative embodiment. Machine learning model 1110 may be a single machine learning model or several connected machine learning models. For example, there may be separate machine learning models for predicting patient needs, determining physiological trends, identifying patient activity trends, predicting energy requirements, prioritizing sensors, scheduling power/recharging to sensors, classifying patient wellness (e.g., requiring emergency services, requiring a visit with a healthcare professional, point-of-care recommendation), and scheduling communication. Some machine learning models may receive as inputs the outputs of other machine learning models. In one embodiment, the machine learning models may be of different types (e.g., classification, regression, clustering, dimensionality reduction, deep learning, etc.) Alternatively, machine learning model 1110 may be a single neural network with multiple output heads.

Machine learning model 1110 receives as input physiological features 1111, activity features 1112, energy features 1113, and patient history features 1114. Physiological features 1111 include sensor data and other patient medical data, such as data from a patient EMR. Physiological features 1111 may be timestamped and tagged with sensor ID, location on body, etc. Physiological features 1111 may include sensor data from all of the sensors associated with the patient. Patient activity features 1112 include patient lifestyle information, such as exercise events, diet information, sleep patterns, etc.

Patient activity features 1112 may also include timestamped geographic location information and calendar events, such as appointments, work schedule, holidays, etc. Patient activity features 1112 may also include sensor data from Internet of Things (IoT) devices, Global Positioning System (GPS) sensors, or the like.

Energy features 1113 include timestamped energy levels of battery energy storage, sensor power usage, and the like. Energy features 1113 may be collected from sensors and other components based on an amount of charge left in batteries. These energy features 1113 may be collected periodically, such as every second, every minute, or every hour. Alternatively, energy features 1113 may be collected whenever there is a charge event, such as a battery low indicator, a charging start event, a charging end event, or a battery full event.

Patient history features 1114 include historical data from a database of medical knowledge, such as EMRs of the patient being monitored and other patients. Patient history features 1114 allows machine learning model 1110 to learn trends from similar patients. For example, machine learning model 1110 may learn that patients with similar physiological features and activity patterns tend to have particular health outcomes, which can be prevented or encouraged with specific point-of-care recommendations.

Machine learning model 1110 generates as output patient needs/trends prediction 1151, patient activity trends prediction 1152, energy requirements prediction 1153, communication/storage requirement predictions 1154, and point-of-care recommendations 1155. Patient needs/trends prediction 1151 include predictions of patient needs based on medical conditions and physiological features 1111 and patient activity features 1112. For example, a patient with diabetes will need to take periodic blood glucose measurements, or a patient with high blood pressure will need to take measurements from a heart rate monitor. Patient needs/trends prediction 1151 may also include predicted trends in physiological parameters. For example, the patient's blood glucose may spike after meals or the patient's heart rate may increase during times the patient typically exercises. These trends may influence the patient's needs.

Patient activity trends 1152 include predictions about the times and days of patient activities, such as sleep, work, exercise, meals, etc. Patient activity trends 1152 may also predict the times and days the patient will be at various locations, such as rooms of the home, work, car, etc. Patient activity trends 1152 allow the multi-sensor health monitoring platform schedule providing power/recharging to the sensors, as well as storage and communication by predicting when the patient will be in range of wireless charging devices and communications devices/services.

Energy requirements predictions 1153 include predictions of energy requirements of sensors and other components of the multi-sensor health monitoring platform. Machine learning model 1110 may analyze energy features 1113 to predict when energy usage is highest for the various sensors and other components, such as communication devices, storage devices, and the like. Based on patient needs/trends 1151, patient activity trends 1152, and energy requirements 1153, the multi-sensor health monitoring platform schedules providing power/recharging to the sensors and other components to ensure the sensors and other components have sufficient power/energy to meet the patient's needs. For instance, if the patient is diabetic and needs to take a blood glucose reading, then the multi-sensor health monitoring platform must schedule recharging of the blood glucose monitor when the patient is near a wired or wireless charger.

In another embodiment, the multi-sensor health monitoring platform may schedule charging of an on-body energy source, such as a battery pack with wired (e.g., Universal Serial Bus (USB)) or wireless charging (e.g., Qi wireless power transfer). The multi-sensor health monitoring platform may then schedule charging of a subset of sensors from the on-body energy source based on a prediction that the subset of sensors will be within a predetermined distance from the on-body energy source.

In yet another embodiment, the multi-sensor health monitoring platform may generate charging recommendations to the patient with instructions to charge particular sensors based on the patient needs 1151, patient activity trends 1152, and energy requirements 1153. The charging recommendations may include instructions to change location such that wearable sensors are within range of a wireless charger, instructions to connect a sensor or other component to a wired charger, to change a battery on a sensor, to swap out a disposable sensor, or to place a sensor on a charging pad, for example.

Communication/storage requirement predictions 1154 include predicted times and days that sensor data must be stored locally or communicated to the cloud or to a healthcare provider. Some sensor data may be stored locally and provided to a healthcare provider before a doctor visit. Other sensor data may be uploaded to the healthcare provider periodically, such as once a day or week. In one embodiment, machine learning model 1110 may predict a likelihood that an emergency event will occur, at which time a communication to emergency services will be required.

In another embodiment, communication/storage requirements 1154 determine when sensor data are to be stored locally and when the stored data must be communicated to a server or to cloud storage. The machine learning model 1110 may predict when the sensor data is likely to be communicated based on patient activity trends 1152 and energy requirements 1153. For example, the machine learning model 1110 may predict when the platform will be connected to Wi-Fi. As another example, the machine learning model 1110 may predict when the communication subsystem will have sufficient power to complete the transfer of sensor data based on energy features 1113. These predictions may be included in communication/storage requirements 1154.

Point-of-care recommendations 1155 include recommendations for patient action. These recommendations 1155 may include calling emergency services, scheduling an appointment with a healthcare provider, performing additional measurements or tests, and the like. Machine learning model 1110 may generate point-of-care recommendations 1155 based on physiological features 1111, activity features 1112, and patient history features 1114. For example, machine learning model 1110 may predict patient outcome based on physiological features 1111 and the outcomes of similar patients in patient history features 1114. In one example, the multi-sensor health monitoring platform may automatically contact emergency services or automatically schedule an appointment with a healthcare professional based on point-of-care recommendations 1155.

Figure 12:
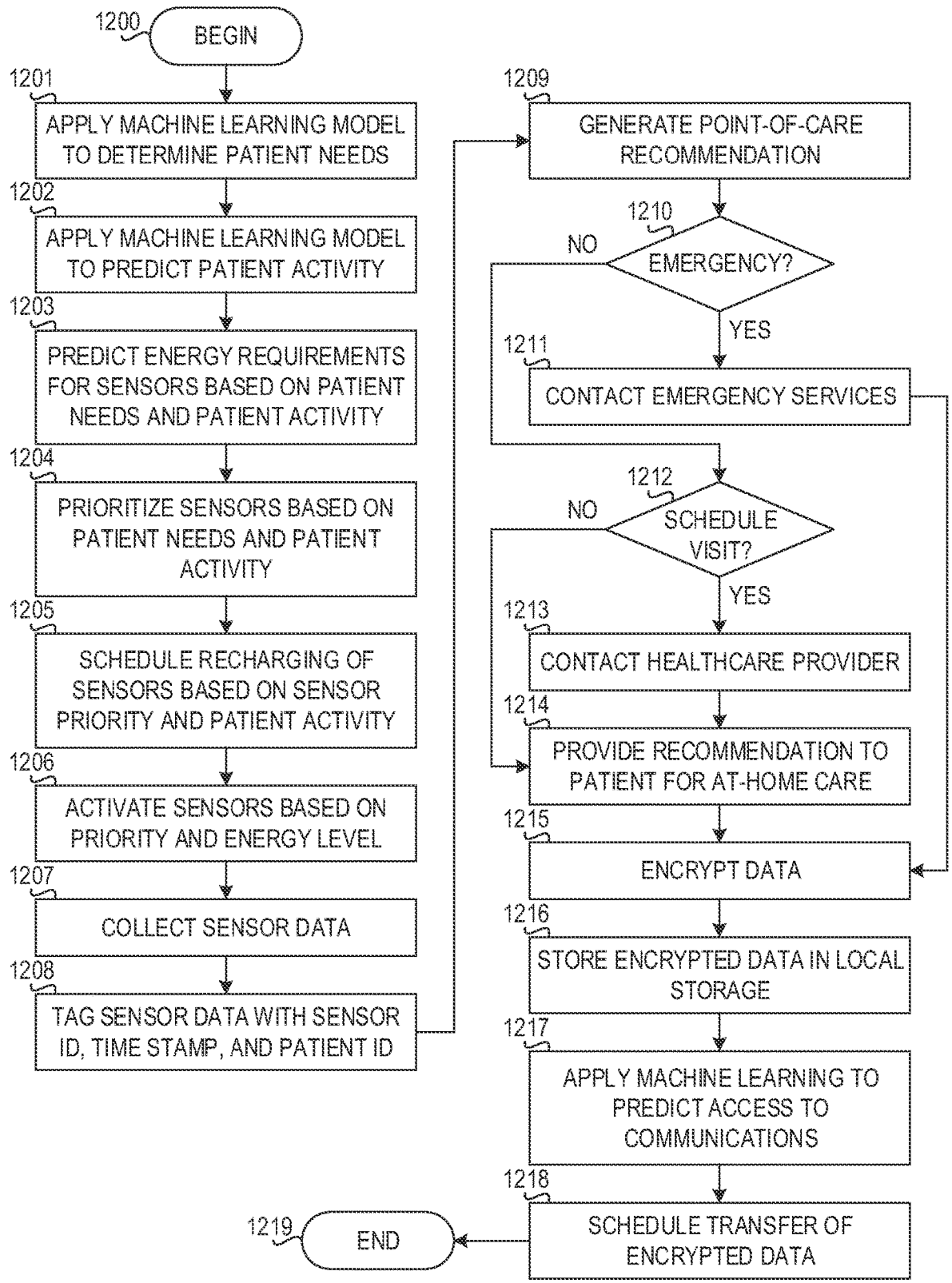
FIG. 12 is a flowchart illustrating operation of a multi-sensor health monitoring platform in accordance with an illustrative embodiment.

FIG. 12 is a flowchart illustrating operation of a multi-sensor health monitoring platform in accordance with an illustrative embodiment. Operation begins (block 1200), and the multi-sensor health monitoring platform applies a machine learning model to determine patient needs (block 1201). The machine learning model is trained to predict patient needs based on physiological features, activity features, and patient history features of the patient being monitored and similar patients. The multi-sensor health monitoring platform applies a machine learning model to predict patient activity (block 1202). The machine learning model is trained to predict patient activity trends based on past patient activity features collected from sensors, such as physiological monitoring sensors, diagnostic tests, Internet of Things (IoT) devices, and the like.

The multi-sensor health monitoring platform applies a machine learning model to predict energy requirements based on patient needs and patient activity (block 1203). The machine learning model is trained to predict energy requirements of sensors and other components based on the times of past measurements, past energy levels, predicted patient needs/trends, and predicted patient activity. The multi-sensor health monitoring platform then prioritizes sensors based on the predicted patient needs and predicted patient activity (block 1204).

The multi-sensor health monitoring platform schedules recharging of the sensors based on sensor priority and patient activity (block 1205). The platform also activates sensors based on the priority and energy level information (block 1206). Then, the multi-sensor health monitoring platform collects sensor data (block 1207) and tags the sensor data with sensor identifiers, time stamp, and patient identifier (block 1208).

The multi-sensor health monitoring platform generates at least one point-of-care recommendation (block 1209). The multi-sensor health monitoring platform determines whether there is an emergency event based on the point-of-care recommendation (block 1210). If there is an emergency event, then the multi-sensor health monitoring platform contacts emergency services (block 1211). Thereafter, operation proceeds to block 1215 to be described below.

If there is not an emergency event in block 1210, then the multi-sensor health monitoring platform determines whether to schedule a visit with a healthcare provider (block 1212). If the platform decides to schedule a visit with a healthcare provider, then the multi-sensor health monitoring platform contacts the healthcare provider (block 1213). Thereafter, or if the platform decides not to schedule a visit with a healthcare provider in block 1212, the multi-sensor health monitoring platform provides the point-of-care recommendation to the patient for at-home care (block 1214).

At block 1215, the multi-sensor health monitoring platform encrypts the tagged sensor data. The multi-sensor health monitoring platform stores the encrypted data in local storage (block 1216). Next, the multi-sensor health monitoring platform applies machine learning to predict access to communications services and devices (block 1217) and schedules transfer of encrypted sensor data (block 1218). Thereafter, operation ends (block 1219).

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication-based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to configure the processor to implement a multi-sensor health monitoring platform, the method comprising:
    applying a machine learning model to predict patient needs and patient activity trends based on physiological features and activity features of the patient;
    applying the machine learning model to predict energy requirements and energy availability for a plurality of medical sensors based on the predicted patient needs and patient activity trends, wherein the predicted energy requirements indicates an amount of energy needed to power a subset of medical sensors, of the plurality of medical sensors, to monitor at least one predicted patient need or activity at a future time point based on the predicted patient needs and patient activity trends, wherein the subset of medical sensors are medical sensors that monitor physiological features or activity features of the patient specific to the at least one predicted patient need or patient activity;
    scheduling recharging of the subset of medical sensors, in the plurality of medical sensors, based on the predicted energy requirements and predicted energy availability of the subset of medical sensors, wherein the scheduling schedules recharging of the subset of medical sensors at a time point prior to the future time point such that the recharging causes at least one power source of the subset of medical sensors to have available electrical power to satisfy the predicted energy requirements at the future time point;
    automatically controlling the plurality of medical sensors based on the predicted patient needs, patient activity trends, and predicted energy requirements, to set the subset of medical sensors to a recharge state in response to a current time being the time point prior to the future time point, to set the subset of medical sensors to an activate state in response to the current time being the future time point, and to set one or more other medical sensors in the subset of medical sensors to an inactive state in response to the current time being the future time point;
    collecting sensor data from the subset of medical sensors in response to the current time being the future time point; and
    applying the machine learning model to generate a point-of-care recommendation based on the collected sensor data.

2. The method of claim 1, wherein the plurality of medical sensors comprise at least one of patient-worn sensors, non-wearable sensors, or internal sensors that are implanted in the patient.

3. The method of claim 1, wherein applying the machine learning model to predict patient needs and patient activity trends comprises applying the machine learning model to patient history features for similar patients, and wherein applying the machine learning model to predict energy requirements for the plurality of medical sensors comprises applying the machine learning model to energy features of past energy usage of the plurality of medical sensors.

4. The method of claim 1, wherein collecting the sensor data comprises tagging the sensor data with one or more sensor identifiers, a time stamp, and a patient identifier.

5. The method of claim 1, wherein applying the machine learning model to generate the point-of-care recommendation comprises at least one of predicting whether an emergency event is occurring or scheduling a visit with a healthcare provider.

6. The method of claim 5, further comprising contacting emergency services responsive to determining that an emergency event is occurring.

7. The method of claim 1, further comprising applying the machine learning model to predict access to a communications device and scheduling transfer of the collected sensor data based on the predicted access to the communications device.

8. The method of claim 1, further comprising training the machine learning model, through a machine learning training process based on historical data comprising data specifying past energy requirements of sensors, past energy levels of sensors, past predicted patient needs, and past predicted patient activity, to predict energy requirements.

9. The method of claim 8, wherein the historical data comprises insight recommendations and outcomes relative to time for a one or more similar patients having characteristics similar to the patient, historical sensor data for the plurality of medical sensors associated with the patient, and patient health records for the patient and one or more similar patients.

10. The method of claim 1, wherein scheduling recharging of the subset of medical sensors comprises selecting a recharge rate and the time point prior to the future time point for automatically initiating recharging of the subset of medical sensors.

11. The method of claim 1, wherein the machine learning model learns which medical sensors in the plurality of medical sensors will be needed at different times of the day based on the patient activity trends and selects the learned medical sensors for inclusion in the subset of medical sensors.

12. The method of claim 1, wherein scheduling recharging of the subset of medical sensors comprises predicting, by the machine learning model, when the patient will be physically in a location of a charger, and wherein the time point prior to the future time point is determined to be a time point when the patient will be physically in the location of the charger.

13. The method of claim 1, wherein scheduling recharging of the subset of medical sensors comprises outputting a charging recommendation output to the patient with instructions to change a physical location of the patient to be within a range of a charger and to charge the subset of medical sensors.

14. The method of claim 1, wherein the machine learning model comprises at least one first machine learning model that is trained to predict the patient needs and the patient activity trends based on the physiological features and the activity features of the patient and one or more similar patients having similar characteristics to the patient, and at least one second machine learning model, different from the at least one first machine learning model, that is trained to predict the energy requirements and energy availability for the plurality of medical sensors based on the predicted patient needs and patient activity trends.

15. A computer program product comprising a non-transitory computer readable medium having a computer readable program stored therein, wherein the computer readable program, when executed on a computing device, causes the computing device to implement a multi-sensor health monitoring platform, wherein the computer readable medium causes the computing device to:
   apply a machine learning model to predict patient needs and patient activity trends based on physiological features and activity features of the patient;
   apply the machine learning model to predict energy requirements and energy availability for a plurality of medical sensors based on the predicted patient needs and patient activity trends, wherein the predicted energy requirements indicates an amount of energy needed to power a subset of medical sensors, of the plurality of medical sensors, to monitor at least one predicted patient need or activity at a future time point based on the predicted patient needs and patient activity trends, wherein the subset of medical sensors are medical sensors that monitor physiological features or activity features of the patient specific to the at least one predicted patient need or patient activity;
   schedule recharging of the subset of medical sensors, in the plurality of medical sensors, based on the predicted energy requirements and predicted energy availability of the subset of medical sensors, wherein the scheduling schedules recharging of the subset of medical sensors at a time point prior to the future time point such that the recharging causes at least one power source of the subset of medical sensors to have available electrical power to satisfy the predicted energy requirements at the future time point;
   automatically controlling the plurality of medical sensors based on the predicted patient needs, patient activity trends, and predicted energy requirements, to set the subset of medical sensors to a recharge state in response to a current time being the time point prior to the future time point, to set the subset of medical sensors to an activate state in response to the current time being the future time point, and to set one or more other medical sensors in the subset of medical sensors to an inactive state in response to the current time being the future time point;
   collect sensor data from the subset of medical sensors in response to the current time being the future time point; and
   apply the machine learning model to generate a point-of-care recommendation based on the collected sensor data.

16. The computer program product of claim 15, wherein applying the machine learning model to predict patient needs and patient activity trends comprises applying the machine learning model to patient history features for similar patients, and wherein applying the machine learning model to predict energy requirements for the plurality of medical sensors comprises applying the machine learning model to energy features of past energy usage of the plurality of medical sensors.

17. The computer program product of claim 15, wherein the computer readable medium causes the computing device to apply the machine learning model to predict access to a communications device and scheduling transfer of the collected sensor data based on the predicted access to the communications device.

18. The computer program product of claim 15, wherein scheduling recharging of the subset of medical sensors comprises predicting, by the machine learning model, when the patient will be physically in a location of a charger, and wherein the time point prior to the future time point is determined to be a time point when the patient will be physically in the location of the charger.

19. An apparatus comprising:
   a processor; and
   a memory coupled to the processor, wherein the memory comprises instructions which, when executed by the processor, cause the processor to implement a multi-sensor health monitoring platform, wherein the instructions cause the processor to:
   apply a machine learning model to predict patient needs and patient activity trends based on physiological features and activity features of the patient;
   apply the machine learning model to predict energy requirements and energy availability for a plurality of medical sensors based on the predicted patient needs and patient activity trends, wherein the predicted energy requirements indicates an amount of energy needed to power a subset of medical sensors, of the plurality of medical sensors, to monitor at least one predicted patient need or activity at a future time point based on the predicted patient needs and patient activity trends, wherein the subset of medical sensors are medical sensors that monitor physiological features or activity features of the patient specific to the at least one predicted patient need or patient activity;
   schedule recharging of the subset of medical sensors, in the plurality of medical sensors, based on the predicted energy requirements and predicted energy availability of the subset of medical sensors, wherein the scheduling schedules recharging of the subset of medical sensors at a time point prior to the future time point such that the recharging causes at least one power source of the subset of medical sensors to have available electrical power to satisfy the predicted energy requirements at the future time point;
   automatically controlling the plurality of medical sensors based on the predicted patient needs, patient activity trends, and predicted energy requirements, to set the subset of medical sensors to a recharge state in response to a current time being the time point prior to the future time point, to set the subset of medical sensors to an activate state in response to the current time being the future time point, and to set one or more other medical sensors in the subset of medical sensors to an inactive state in response to the current time being the future time point;
   collect sensor data from the subset of medical sensors in response to the current time being the future time point; and
   apply the machine learning model to generate a point-of-care recommendation based on the collected sensor data.

20. The apparatus of claim 19, wherein scheduling recharging of the subset of medical sensors comprises predicting, by the machine learning model, when the patient will be physically in a location of a charger, and wherein the time point prior to the future time point is determined to be a time point when the patient will be physically in the location of the charger.

\* \* \* \* \*